(12) United States Patent
Palatnik et al.

(10) Patent No.: US 6,654,621 B2
(45) Date of Patent: Nov. 25, 2003

(54) FINGER OXIMETER WITH FINGER GRIP SUSPENSION SYSTEM

(75) Inventors: Sam Palatnik, Glendale, WI (US); Dave Donars, New Berlin, WI (US); Robert Rammel, Muskego, WI (US)

(73) Assignee: BCI, Inc., Waukesha, WI (US)

( * ) Notice: Subject to any disclaimer, the term of this patent is extended or adjusted under 35 U.S.C. 154(b) by 0 days.

(21) Appl. No.: 09/940,418

(22) Filed: Aug. 29, 2001

(65) Prior Publication Data

US 2003/0045784 A1 Mar. 6, 2003

(51) Int. Cl.$^7$ .................................................. A61B 5/00
(52) U.S. Cl. ..................... 600/322; 600/323; 600/340; 600/344
(58) Field of Search .................... 600/322, 323, 600/340, 344, 485, 490, 499

(56) References Cited

U.S. PATENT DOCUMENTS

| | | |
|---|---|---|
| 4,685,464 A | 8/1987 | Goldberger et al. |
| 4,824,242 A | 4/1989 | Frick et al. |
| 4,825,872 A * | 5/1989 | Tan et al. .................. 600/344 |
| 5,035,243 A * | 7/1991 | Muz .......................... 600/344 |
| 5,111,817 A | 5/1992 | Clark et al. |
| 5,247,931 A | 9/1993 | Norwood |
| 5,311,865 A | 5/1994 | Mayeux |
| 5,313,940 A | 5/1994 | Fuse et al. |
| 5,339,810 A | 8/1994 | Ivers et al. |
| 5,438,986 A | 8/1995 | Disch et al. |
| 5,490,523 A | 2/1996 | Isaacson et al. |
| 5,551,423 A | 9/1996 | Sugiura |
| 5,676,139 A | 10/1997 | Goldberger et al. |
| 5,788,634 A | 8/1998 | Suda et al. |
| 5,792,052 A | 8/1998 | Isaacson et al. |
| 5,800,349 A | 9/1998 | Isaacson et al. |
| 5,810,724 A | 9/1998 | Gronvall |
| 5,839,439 A | 11/1998 | Nierlich et al. |
| RE36,000 E | 12/1998 | Swedlow et al. |
| 5,842,981 A | 12/1998 | Larsen et al. |
| 5,957,840 A | 9/1999 | Terasawa et al. |
| 5,961,450 A | 10/1999 | Merchant et al. |
| 5,995,856 A | 11/1999 | Mannheimer et al. |
| 5,995,858 A | 11/1999 | Kinast |
| 6,006,120 A | 12/1999 | Levin |
| 6,041,247 A | 3/2000 | Weckstrom et al. |
| 6,045,511 A | 4/2000 | Ott et al. |
| 6,083,156 A | 7/2000 | Lisiecki |
| 6,115,621 A | 9/2000 | Chin |
| 6,151,516 A | 11/2000 | Kiani-Azarbayjany et al. |
| 6,154,667 A | 11/2000 | Miura et al. |
| 6,163,715 A | 12/2000 | Larsen et al. |
| 6,173,196 B1 | 1/2001 | Delonzor et al. |
| 6,178,343 B1 | 1/2001 | Bindszus et al. |
| 6,181,959 B1 | 1/2001 | Schollermann et al. |
| 6,226,539 B1 | 5/2001 | Potratz |
| 6,236,037 B1 | 5/2001 | Asada et al. |

* cited by examiner

*Primary Examiner*—Eric F. Winakur
*Assistant Examiner*—David J. McCrosky
(74) *Attorney, Agent, or Firm*—Louis Woo

(57) ABSTRACT

A finger oximeter has a fixed first finger grip member and a second finger grip member that is movable relative to the first fixed finger grip member. The finger grip members are mounted to a casing, with the first finger grip member being fixedly coupled to a top portion of the casing and the second finger grip member being movable vertically within the casing. A force is continuously applied against the movable finger grip member to bias it towards the fixed finger gripping member. This biasing force has sufficient yield so that when a finger is inserted between the two finger grip members, the movable finger grip member would yield to the incoming finger. At the same time the biasing force is of a sufficient magnitude to push the movable finger grip member towards the fixed finger grip member to effect a firm grip of the finger. The biasing force is evenly distributed to the movable finger grip portion to effect a floating finger grip suspension system for the finger oximeter.

30 Claims, 3 Drawing Sheets

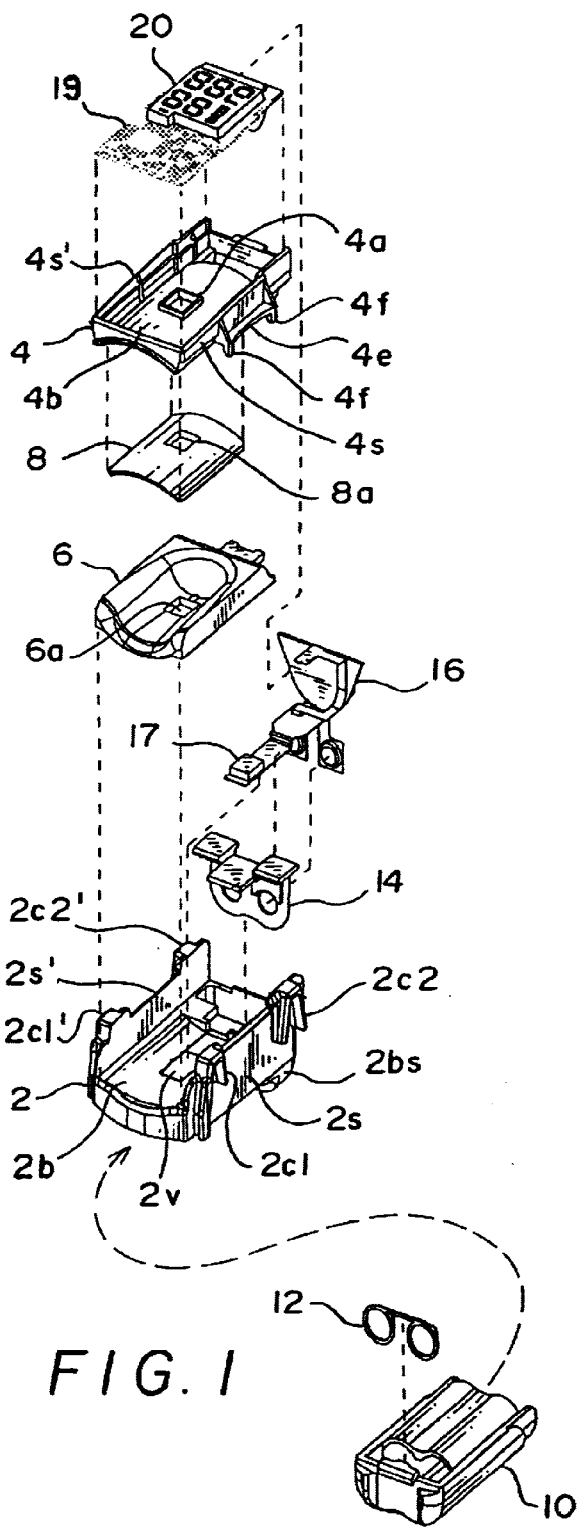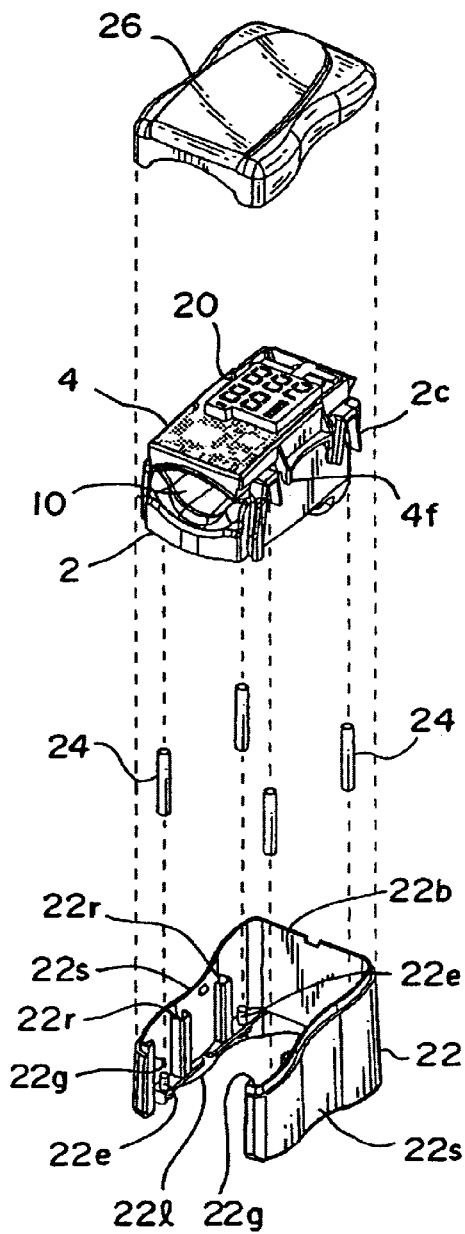
FIG. 1
FIG. 2

FINGER OXIMETER WITH FINGER GRIP SUSPENSION SYSTEM

FIELD OF THE INVENTION

The present invention relates to finger oximeters and more particularly to a finger oximeter having a suspension system that enables the finger gripping portions of the oximeter to firmly and evenly grasp a patient's finger.

BACKGROUND OF THE INVENTION

There are a number of known finger oximeters. Generally, these finger oximeters are pulse oximetry units that utilize a sensor, and a coacting photodetector that detects the light emitted by the sensor, for determining the blood oxygen saturation of the arterial blood passing through the finger of a subject. To illuminate the finger of the subject, and to detect the light passing through the subject's finger, a prior art finger oximeter usually would have a finger gripping mechanism that has two finger gripping portions. The prior art teaches that these finger gripping portions hingedly coact with each other, usually by pivots. The following U.S. patents specifically disclose finger gripping portions that open to accept a finger via some hinge mechanism that enables the finger gripping portions of the finger oximeter to pivot about one end point of the finger oximeter: U.S. Pat. Nos. 4,685,464; 5,490,523; 5,792,052; 5,313,940; 5,676,139; 5,810,724; 5,957,840; and 6,041,247.

There are other methods of enclosing two finger gripping portions about a finger. One such method is the taping of a finger to a photodetector by means of a tape that has a light emitter, as disclosed in U.S. Pat. No. 5,209,230. Another method clamps two finger gripping portions together by means of coacting teeth at the respective sidewalls of the finger gripping portions. This is disclosed in U.S. Pat. No. 5,339,810. The use of a single piece U-shaped flexible holder that expands with the insertion of a finger is disclosed in U.S. Pat. No. 5,311,865.

For those finger oximeters that use two piece finger gripping portions which are tightened by coacting grasping teeth at their respective sidewalls, there is the disadvantage that it is difficult to remove the finger from the finger gripping portions since the finger gripping portions are locked at a given dimension. And for those finger oximeters that utilize a hinged pivoting mechanism, the force that the finger gripping portions applies to a finger tends to be uneven along the finger, and gets weaker the further the finger is away from the hinged location.

SUMMARY OF THE PRESENT INVENTION

The present invention finger oximeter has a floating suspension system that results from one of the finger gripping portions being movable vertically relative to the other finger gripping portion, which is fixed. A biasing force is applied against the movable finger gripping portion so that the movable finger gripping portion is constantly biased towards the fixed finger gripping portion. The two coacting finger gripping portions are configured such that their opposing surfaces are contoured to form an opening for accepting a finger inserted therebetween. The biasing force applied against the movable finger gripping portion is such that the movable finger portion is yieldable when a finger is inserted between the fixed and movable finger portions, and yet at the same time has a sufficient large biasing force to push the movable finger portion towards the fixed finger gripping portion with an even distribution of force along the length of the finger, to thereby cause the two finger gripping portions to firmly grasp the finger placed therebetween.

The force applied against the movable finger gripping portion to bias it towards the fixed finger gripping portion is supplied by a plurality of coiled springs interposed between the movable finger gripping portion and a casing along which sidewalls the movable finger gripping portion guidingly moves. The springs may be secured to ledges extending from the lower portion of the respective sidewalls of the casing so that the biasing force is applied against the movable finger gripping portion in such a way that the movable finger gripping portion is movable vertically with respect to the fixed finger gripping portion.

The fixed finger gripping portion may be mounted to the upper part of the casing, and is configured such that its upper surface is adaptable to receive a printed circuit board that has mounted thereto or etched thereon a number of electronic components or circuits that effect the operation of the finger oximeter. A display, LED or otherwise, is also mounted to the PC circuit board for displaying values that represent the physical parameters of the patient measured via the patient's finger.

The finger gripping portions are further configured to have respective apertures through which light from a light emitter may be directed from one of the finger gripping portions to a corresponding aperture of the other finger gripping portion, which is equipped with a receptive photodetector.

To power the finger oximeter of the instant invention, a battery pack or module is mounted to the underside of the movable finger gripping portion so as to move in unison with the movable finger gripping portion. To operate, a user needs to manually activate a switch mounted to the casing. To conserve energy, the device is automatically turned off after a predetermined time period, if it no longer is in use.

It is therefore an objective of the present invention to provide a finger oximeter that has a floating suspension system.

The finger oximeter of the instant invention has the further objective of evenly distributing the gripping force applied by its finger gripping portions to the being gripped finger.

BRIEF DESCRIPTION OF THE DRAWINGS

The above-mentioned objectives and advantages of the instant invention will become apparent and the invention itself will be best understood by reference to the following description of an embodiment of the invention taken in conjunction with the accompanying drawings, wherein:

FIG. 1 is a perspective drawing that shows various components of the finger oximeter of the instant invention being in various superposed positions;

FIG. 2 is a perspective view illustrating the various components shown in FIG. 1 as well as the coil springs, the casing and the cover of the device being in alignment with each other;

DETAILED DESCRIPTION OF THE INVENTION

Figure 3B:
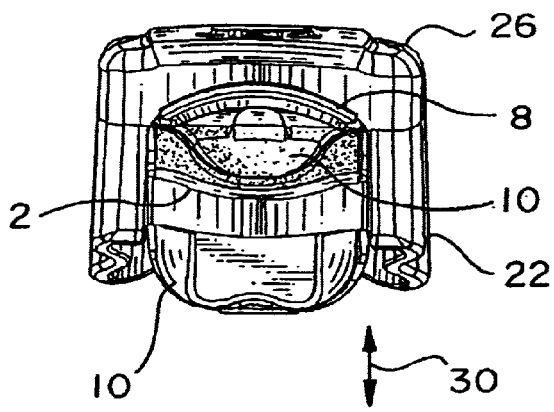
FIG. 3B is a front view of the finger oximeter of the instant invention that shows the opening through which a finger may be inserted between the two finger gripping portions of the device.

With reference to FIG. 1, the finger oximeter of the present invention is shown to include a lower finger grip portion 2 and an upper finger grip portion 4. Fitted to lower finger grip portion 2 and upper finger grip portion 4 are lower finger pad 6 and upper finger pad 8, respectively. The lower and upper finger grip portions, as well as their finger pads, are configured to conform to the shape of a human digit, such as for example a finger. This is best illustrated by the lower surface of finger pad 6 and the upper surface of finger pad 8, which are opposed to each other. Thus, once the respective finger pads 6, 8 are attached to their corresponding finger grip portions 2, 4, an opening 10, best shown in FIGS. 2 and 3B, is provided when finger grip portions 2 and 4 are positioned adjacent to each other.

As best shown in FIG. 1, lower grip finger portion 2 is an elongate member that has two sides 2s extending from a base 2b. A space or void 2v is provided at approximately the center of base 2b onto which a photodetector 18 (D1 in FIG. 4) may be positioned. The front end of base 2b is curved for forming one portion of opening 10. The back end of elongate member 2 has a backstop 2bs that is configured to receive, in a sliding engagement fashion, a battery module 10. Although not shown, battery module 10 is configured to enable the insertion of two batteries thereinto for providing power to the electronic components shown in FIG. 4 to thereby energize the finger oximeter, whose operation will be discussed later. A spring-like conductor 12 inserted to battery module 10 connects in series the batteries, thereby increasing the available voltage.

Each of sidewalls 2s of elongate member 2 further has extending therefrom at least two ears, or catches 2c1 (2c1') and 2c2 (2c2'). The purpose of catches 2c will be discussed with reference to FIG. 2.

Lower finger pad 6, which may be made of a rubbery material that is not compliant, is attached to base 2b of finger grip portion 2. In addition to finger pad 6, a conductive strip 14 is inserted to the back end of finger grip portion to provide an electrical path for the power supplied by battery module 10. Connected to conductive end 14 is a flexible strip 16 which has attached thereto photodetector 17. With photodetector 17 resting in space 2v of elongate member 2 and with finger pad 6 placed thereover, photodetector 17 is exposed, and is therefore adaptable to receive light directed thereto, per aperture 6a of finger pad 6. As can be seen, finger pad 6 is configured, per its arcuate interior surface, to conform partially to the shape of a human finger.

Upper finger grip portion 4, which is also configured in the form of an elongate member, has attached to its underside finger pad 8, which is curved in an opposing manner to finger pad 6 and contoured to partially conform to the shape of a finger. Finger pad 8, also made of a non-compliant rubber material, may be attached to the lower surface of elongate member 4 by glue or other adhesive means, which is similar to the way by which finger pad 6 is attached to elongate member 2. Once attached, aperture 8a of finger pad 8 is aligned with aperture 4a of elongate member 4.

Elongate member 4 has two sides 4s extending upwards from its base 4b to form a semi-closed enclosure at its upper surface for accepting a printed circuit board or module 19. Although not shown clearly, mounted to module 19 are a number of electronic components, the circuitries of which are shown in detail in FIG. 4. Extending from each side 4s of elongate member is an extension 4e that has two fingers 4f pointing downwards. The purpose of extensions 4e will be discussed with respect to FIG. 2. Also mounted to module 19 is a display 20 that includes a number of digits for displaying information that corresponds to the physical parameters of a patient, such as for example the blood oxygen saturation of arterial blood, as measured from the patient's finger being inserted between finger grip portions 2 and 4. To effect the measurement of the physical attribute of the patient, a light source, such as for example a light emitting diode, is mounted to the underside of module 19 to be in alignment with aperture 4a of elongate member 4. The power provided to module 19 comes from the flexible conductive strip 16.

With reference to FIG. 2, the various components illustrated in FIG. 1 of the finger oximeter of the instant invention are shown as having been assembled, with upper finger grip portion 4 being adjacent to lower finger grip portion 2. As was mentioned previously, when in such close contact, opening 10 is formed at the front of the two finger gripping members. It is through this opening that a finger is placed between the finger grip portions 2 and 4.

As further shown in FIG. 2, the in contact finger grip portions 2, 4 are superposed over a casing 22, which has the form of a U-shaped skirt. Casing 22 has a back wall 22b and two sidewalls 22s. Extending from the lower portion of sidewalls 22s are respective ledges 22l. In the inside of the respective sidewalls 22s are receptacles 22r, which are configured to receive fingers 4f of extension 4e of upper finger grip portion 4. Upon insertion of fingers 4f to receptacles 22r, finger grip portion 4 is fixedly coupled to the top or upper part of casing 22. An adhesive may be used to further ensure that upper finger grip portion 4 is fixedly coupled to casing 22.

At the two distal ends of sides 22s there are formed respective gripping edges or fingers 22g. Formed at the respective ledges 22l are a number of fingers or extensions 22e that provide the respective anchors each for securely receiving a corresponding spring 24. As shown, there are four springs 24, each securedly anchored by one of the extensions 22e at one corner of casing 22. Springs 24 may each be conventional compression coil springs.

As further shown in FIG. 2, once anchored to extensions 22e, when lower finger grip portion 2 is inserted to casing 22, each of catches 2c in the form of ears extending from sidewalls 2s of elongate member 2 catches and presses down on a corresponding spring 24. Springs 24 are chosen to have a given elasticity so that, in combination, those springs provide a biasing force against elongate member 2 in an upwards direction, with reference to upper finger grip portion 4, which is fixedly attached to the upper part of casing 22. Thus, once elongate member 4 is fixedly coupled to casing 22, elongate member 2 nonetheless remains movable relative to elongate member 4, and is guidedly movable along the respective sidewalls 22s of casing 22.

Given the fact that elongate member 2 is supported by independent springs 24 at different locations along its sidewalls 2s, when a finger is inserted to opening 10, although giving way to the finger, the biasing force exerted by springs 24 would act against elongate member 2 vertically so as to firmly bias elongate member 2 against the inserted finger, to thereby firmly grip the inserted finger against fixed elongate member 4. Further, by providing springs 24 at the four corners of elongate member 2, a four point suspension system is effected to evenly distribute across elongate member 2 the biasing force. Accordingly, a finger gripped by elongate members 2 and 4 is gripped evenly along its length. Furthermore, by hiding the springs at the respective corners of casing 22 and elongate member 2 so that no support base is required for elongate member 2, the respective sizes of the case 22 and elongate member 2 could be reduced, thereby leading to a reduction in the size of the entire device. So, too, by hiding the springs between the respective sidewalls of casing 22 and elongate member 2, the springs are sealed from dirt and isolated from potential mechanical abuse.

Although only four springs are shown in the being discussed embodiment, it should be appreciated that a three spring configuration, with one spring at each sidewall and one spring at the back wall of casing 22 may also be used. Conversely, a greater number of springs, with more than two springs along each sidewall of casing 22, may also be used in other embodiments of the instant invention.

To complete the assembled device of the instant invention, a filtered cover 26 that allows the digits to be seen from display 20, is placed over elongate member 4 so as to be fixedly coupled either to elongate member 4 or to the upper edges of casing 22.

Figure 3A:
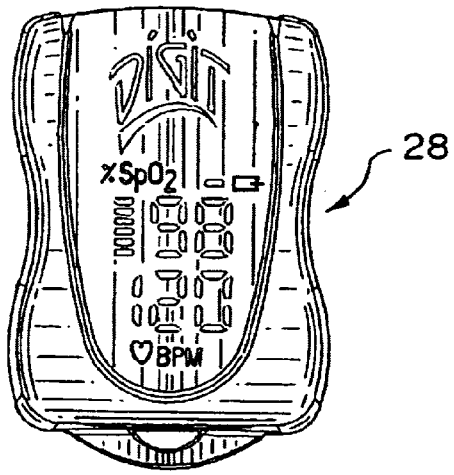
FIG. 3A is a top view of an assembled device of the instant invention.

With reference to FIGS. 3A–3D, different views of the assembled finger oximeter of the instant invention is shown. FIG. 3A shows a plan view of the assembled device 28, with the digits displaying the blood oxygen saturation, and also the heart rate that may be obtained by measuring the physical attributes of a patient by means of her finger.

FIG. 3B is a front view of the device showing opening 10 through which the finger of a patient is inserted. As further shown, upper finger grip portion 4 is protected by cover 26 so that only a portion thereof, and a portion of finger pad 8, are shown. However, movable finger grip portion 2 is shown to be mounted within casing 22, with battery module 10 removably coupled to the underside thereof. Movable finger grip member 2, which, in response to the bias force supplied by springs 24, is movable bidirectionally as indicated by directional arrow 30.

Figure 3D:
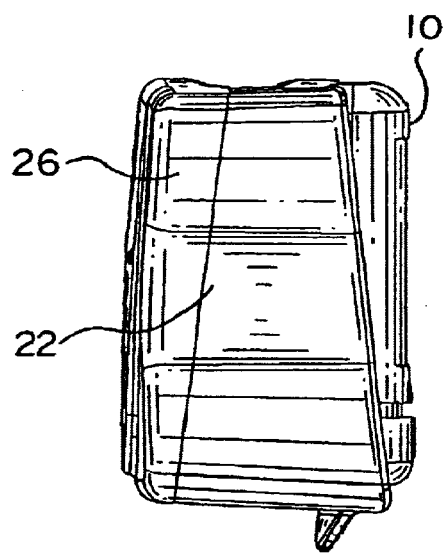
FIG. 3D is a side view of the FIG. 3A device.
Figure 3C:
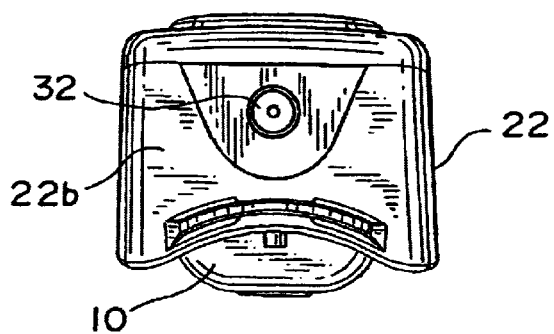
FIG. 3C is a back view of the finger oximeter of the instant invention.

FIG. 3C shows the back side of the finger oximeter of the instant invention. As shown, casing 22, or rather the back walls 22b thereof, has mounted thereto a switch 32, which enables a user to manually activate the device, i.e., by energizing the electronic components mounted to circuit board 18. The back side of battery module 10 is also shown in FIG. 3C.

FIG. 3D is a side view of device 28 of the instant invention which shows cover 26 attached to casing 22. Battery pack 10 is shown to form the bottom base of the device.

Figure 4:
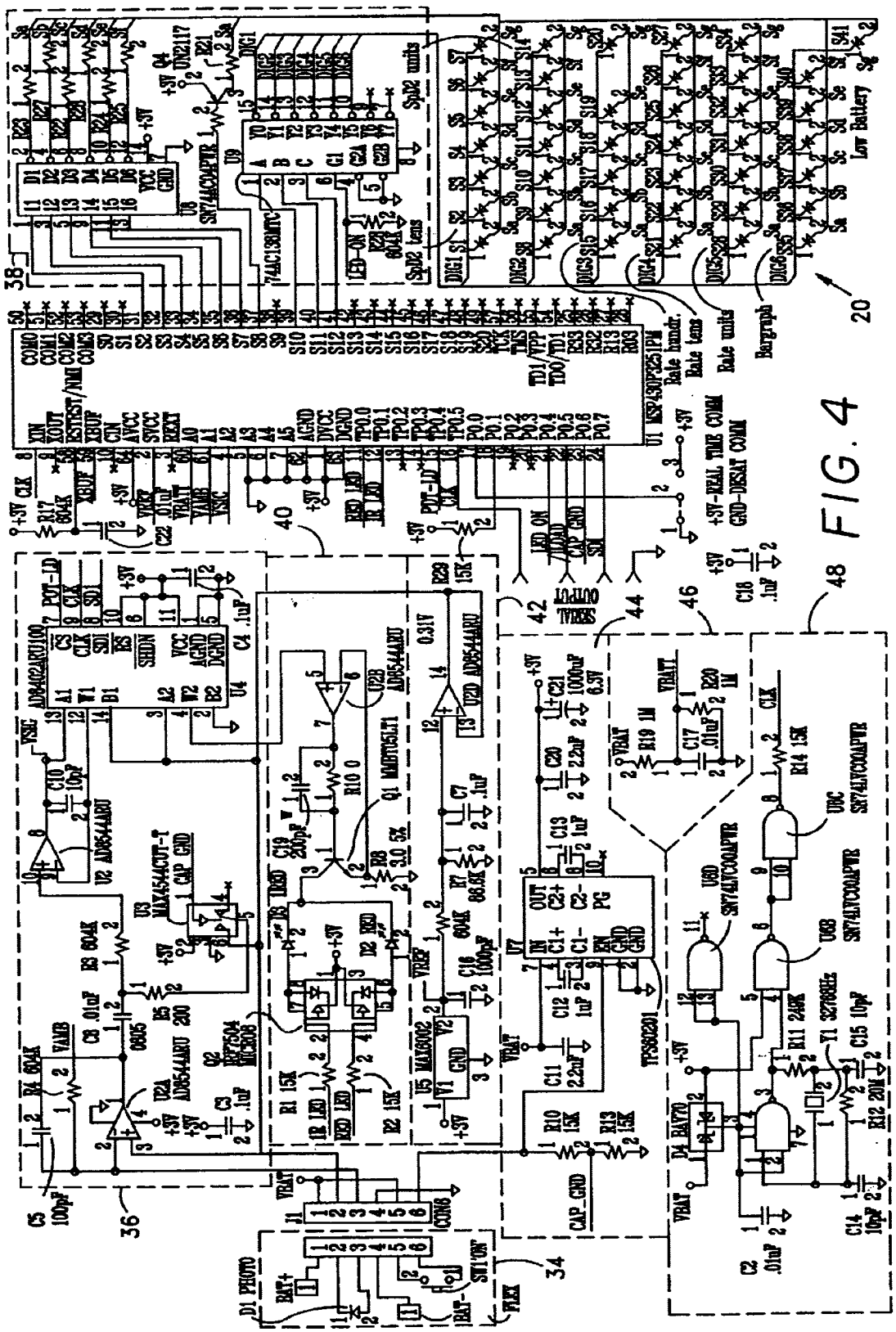
FIG. 4 is an electrical schematic of the finger oximeter of the instant invention.

FIG. 4 is a schematic of the electronic circuitry representative of the electronic components mounted to circuit board 18 of the device. For ease of discussion, the various major functions of the circuitry of the instant invention device are separately grouped together by dotted lines. In particular, as shown in dotted box 34, a photodiode D1 (18 in FIG. 1) is mounted onto a flexible circuit support strip that is fitted to space 2v of lower grip member 2. Switch SW1, also mounted to and in electrical connection to the flexible circuit strip 34, when turned on by the user, causes light from the LED in circuit 40 to be directed to the finger placed between the finger grip portions 2 and 4. Once the finger is removed from the finger grip portions, microprocessor U1 is programmed to turn off device 28 after a predetermined time period, for example 8 seconds, so as to conserve energy.

The photodetector and switch SW1 are connected to the main circuit by means of a conventional coupling. In particular, circuit 34 mounted on the flexible strip is connected to functional circuit 36, which is an analog detector pre-conditioning circuit. As shown, the input electrical current signal measured from the finger of the patient is sent to an op amp U2A, where the analog current signal is converted to an analog voltage signal. The analog voltage signal is amplified by op amp U2C to output an amplified analog voltage signal VSIG. The dynamic range of the signal is controlled by IC circuit U4, which in essence is an integrated digital potentiometer.

The amplified analog voltage signal VSIG is input to microprocessor U1 at input A2. This analog voltage signal is converted by microprocessor U1 to a corresponding digital signal and output to circuit 38, which is a LED driver circuit comprising driver IC circuits U8 and U9. The driver circuit 38 provides the signal to the various digits DIG1–DIG6 for displaying the information collected from the patient on display 20.

Another major functional component of the circuitry of FIG. 4 includes circuit 40, which is a variable LED driver circuit that drives the two LEDs that emit the light directed to the finger of the patient through apertures 4a and 8a of the upper finger grip portion and the upper finger pad 8, respectively. The light, after diffusing through the finger of the patient, is sensed by photodetector D1 (18), which in turn outputs the resulting current signal to analog detector pre-conditioning circuit 36.

Sub-circuit 44 of the FIG. 4 circuitry is a switching power supply circuit that regulates the power to be supplied to the various components of the FIG. 4 circuitry.

Circuit 46 is a battery measurement voltage divider circuit that identifies when the voltage from battery pack 10 is low.

Circuit 48 is a timing circuit for the components of the finger oximeter of the instant invention. A clock pulse is generated from circuit 48 for microprocessor U1 by component U6A. Components U6B and U6C in combination ensure that there is enough voltage from battery pack 10 if the voltage output is less than 3 volts, so that the appropriate clocking signals are provided for the various components of the circuitry of FIG. 4.

The present invention is subject to many variations, modifications and changes in detail. For example, instead of springs 34 being anchored to extensions 22e of ledges 22l of casing 22, the biasing mechanism for lower grip portion 2 could be an elastic one piece spring mechanism such as a leaf spring that biases elongate member 2 against the sidewalls 22s, and/or back wall 22b of casing 22. To anchor such leaf spring to the casing, the ledges at the base of the casing may have to be expanded. So, too, could an elastic material such as rubber that has sufficient biasing characteristics be used to keep a force biasing movable elongate member 2 towards fixed elongate member 4. Thus, it is intended that all matter described throughout this specification and shown in the accompanying drawings be interpreted as illustrative only and not in a limiting sense. Accordingly, it is intended that the invention be limited only by the spirit and scope of the hereto appended claims.

What is claimed is:

1. A finger oximeter, comprising:
 a casing having a back wall and two sidewalls each extending from said back wall;
 a first finger portion sandwiched by and movable vertically along said sidewalls;
 a second finger portion in fixed relation with said casing to form an upper stop for the movement of said first finger portion;

wherein the respective surfaces of said first and second finger portions facing each other are configured to conform to a finger placed therebetween; and spring means provided at said casing for applying a biasing force against said first finger portion so that a finger placed between said first and second finger portions is firmly gripped by said first and second finger portions due to said first finger portion being biased by said spring means towards said second finger portion.

2. Finger oximeter of claim 1, wherein each of said sidewalls of said casing comprises a ledge for forming a barrier to prevent said first finger portion from falling out of said casing, each of said sidewalls guiding the vertical movement of said first finger portion; and wherein said spring means comprises a plurality of springs at least two of which being secured to opposite ends of the ledge of each of said sidewalls for supporting and applying said biasing force vertically against said first finger portion.

3. Finger oximeter of claim 1, further comprising:

a printed circuit board having mounted thereon a plurality of electronic circuit components coupled to the top of said second finger portion, said second finger portion having an aperture for enabling the light from a light emitting source mounted to said circuit board to be directed toward said finger gripped by said first and second finger portions;

a display mounted on top of said circuit board for displaying at least readings of blood oxygen saturation of arterial blood measured from said finger; and a cover positioned over said display and fixedly coupled to either said second finger portion or the top of said casing.

4. Finger oximeter of claim 3, further comprising:

a battery module removably coupled to the underside of said fist finger portion for supplying power to said electronic circuit components and said display.

5. Finger oximeter of claim 3, further comprising:

a switch mounted to said casing to enable a user to manually activate said electronic circuit components.

6. A pulse oximeter, comprising:

a fixed portion;

a non-fixed portion movable vertically relative to said fixed portion, said fixed and non-fixed portions in combination providing an opening through which a finger is insertable; arid means biasing against said non-fixed portion to apply a continuously distributed force against said non-fixed portion so that when a finger is inserted between said fixed and non-fixed portions, said non-fixed portion is movable vertically in a planar relationship to said fixed portion to accommodate but yet firmly grip said finger between said fixed and non-fixed portions.

7. Pulse oximeter of claim 6, further comprising:

a casing having two sidewalls extending from a back wall, said fixed portion being sandwiched by and in fixed relation with the upper parts of said sidewalls, said non-fixed portion being sandwiched by said sidewalls and movable vertically along the opposing surfaces of said sidewalls, respective ledges extending from the respective lower parts of said sidewalls forming a base support for said non-fixed portion.

8. Pulse oximeter of claim 7, wherein said biasing means comprises a plurality of springs, at least two of said springs being secured to each of the ledges at a given distance away from each other to provide an evenly distributed biasing upward support force for said non-fixed portion, so that when a finger is inserted between said fixed and non-fixed portions, said non-fixed portion is movable vertically relative to said fixed portion with said non-fixed portion continuously being forced upward against said finger to thereby maintain a firm grip on said finger.

9. Pulse oximeter of claim 8, wherein said springs are compression coil springs.

10. Pulse oximeter of claim 7, further comprising a circuit board coupled to the upper surface of said fixed portion, electronic components and a display being mounted to said circuit board, said fixed portion having an aperture through which a light from a light emitting device electrically connected to said circuit board passes for illuminating a finger placed below said fixed portion, a cover being placed over said circuit board and fixedly coupled to said casing.

11. Pulse oximeter of claim 10, further comprising a battery module removably coupled to the underside of said non-fixed portion for supplying power to said electronic circuit components and said display.

12. Pulse oximeter of claim 10, further comprising a switch mounted to said casing to enable a user to manually activate said electronic circuit components to measure the blood oxygen saturation of arterial blood from said finger gripped by said fixed and non-fixed portions.

13. Pulse oximeter of claim 6, wherein said fixed portion and said non-fixed portions are respective elongate members with respective opposing surfaces positioned in alignment with each other, said pulse oximeter further comprising:

respective finger pads each attached to a corresponding opposing surface of said elongate members, said finger pads are configured to follow the contour of a finger so as to enhance the gripping of a finger placed between said finger pads.

14. Apparatus for gripping a finger, comprising:

first grip means;

second grip means opposing said first grip means, said first and second grip means having respective surfaces facing each other being contoured to enable the gripping of a finger placed therebetween;

wherein one of said first and second grip means is fixed while the other of said first and second grip means is movable vertically relative to said one fixed grip means; and bias means evenly and continuously forcing said movable grip means to move vertically towards said fixed grip means so that a finger remains firmly and evenly gripped by said first and second grip means once it is placed therebetween.

15. Apparatus of claim 14, further comprising a casing having two sidewalls extending from a back wall, said one fixed grip means being sandwiched by and in fixed relation with the upper parts of said sidewalls, said movable grip means being sandwiched by said sidewalls and movable vertically along the opposing surfaces of said sidewalls, respective ledges extending from the respective lower parts of said sidewalls;

wherein said bias means comprises a plurality of springs at least two of which being interposed between each of said ledges and a corresponding opposite side of said movable grip means, said springs providing a biasing force against said movable grip means.

16. Apparatus of claim 15, further comprising a switch mounted to said back wall to enable a user to manually activate electronic circuit components mounted to said one fixed grip means.

17. Apparatus of claim 14, wherein said first and second grip means comprise respective one and other elongate members each having top and bottom surfaces, said elongate members being in alignment with each other so that the bottom surface of said one elongate member faces the top surface of said other elongate member, said elongate members having respective apertures, and respective finger pads each attached to a corresponding one of said bottom surface of said one elongate member and the top surface of said other elongate member, said finger pads being configured to conform to the contour of a finger, each of said finger pads having an aperture in alignment with the apertures of said one and other elongate members.

18. Apparatus of claim 17, further comprising a casing having two sidewalls extending from a back wall, said one elongate member being sandwiched by and fixedly coupled to the upper parts of said sidewalls, said other elongate member being sandwiched by said sidewalls and movable vertically along the opposing surfaces of said sidewalls, respective ledges extending from the respective lower parts of said sidewalls, said bias means comprising a plurality of springs at least two of which being interposed between each of said ledges and a corresponding one of respective ears extending from opposite sides of said other elongate member, said springs functioning as a suspension system for said other elongate member.

19. Apparatus of claim 17, further comprising electronic components and a display mounted on a circuit board coupled to the top surface of said one elongate member, a light emitting source outputting a light through the respective apertures of said one elongate member and the finger pad attached to the bottom surface of said one elongate member, a light detector in alignment with the respective apertures of said other elongate member and the finger pad attached to the top surface of said other elongate member for receiving the light output from said light emitting source passing through the finger gripped by said finger pads.

20. Apparatus of claim 19, further comprising a battery module removably coupled to the bottom surface of said other elongate member so as to move in unison with said other elongate member, said battery module supplying power to said electronic components and said display.

21. A pulse oximeter, comprising:
   a fixed portion;
   a non-fixed portion movable vertically relative to said fixed portion, said fixed and non-fixed portions in combination providing an opening through which a finger is insertable; and
   a plurality of spring members applying a continuously distributed biasing force against said non-fixed portion so that when a finger is inserted to said opening, said non-fixed portion is movable vertically in planar relationship to said fixed portion to accommodate and grip said finger between said fixed and non-fixed portions.

22. Pulse oximeter of claim 21, further comprising:
   a casing having two sidewalls extending from a back wall, said fixed portion being sandwiched by and in fixed relation with the upper parts of said sidewalls, said non-fixed portion being sandwiched by said sidewalls and movable vertically along the opposing surfaces of said sidewalls, respective ledges extending from the respective lower parts of said sidewalls forming a base support for said non-fixed portion.

23. Pulse oximeter of claim 22, wherein at least two of said spring members being secured to each of the ledges at a given distance away from each other to provide an evenly distributed biasing upward support force for said non-fixed portion.

24. Pulse oximeter of claim 22, further comprising a switch mounted to said casing to enable a user to manually activate said electronic circuit components to measure the blood oxygen saturation of arterial blood from said finger gripped by said fixed and non-fixed portions.

25. Pulse oximeter of claim 21, further comprising a circuit board coupled to the upper surface of said fixed portion, electronic components and a display being mounted to said circuit board, said fixed portion having an aperture through which a light from a light emitting device electrically connected to said circuit board passes for illuminating a finger placed below said fixed portion.

26. A pulse oximeter, comprising:
   a fixed portion;
   a non-fixed portion movable vertically relative to said fixed portion, said fixed and non-fixed portions in combination providing an opening through which a digit is insertable; and
   a suspension system for supporting said non-fixed portion relative to said fixed portion, said suspension system enabling said non-fixed portion to have a continuous force evenly distributed there against so that said non-fixed portion is movable vertically in planar relationship to said fixed portion to accommodate but yet hold firmly between said fixed and non-fixed portions said digit inserted to said opening.

27. Pulse oximeter of claim 26, wherein said suspension system comprises a multiple point suspension system having at least two spring members applying a bias force against said non-fixed member.

28. Pulse oximeter of claim 26, further comprising:
   a casing having two sidewalls extending from a back wall, said fixed portion being sandwiched by and in fixed relation with the upper parts of said sidewalls, said non-fixed portion being sandwiched by said sidewalls and movable vertically along the opposing surfaces of said sidewalls, respective ledges extending from the respective lower parts of said sidewalls forming a base support for said non-fixed portion.

29. Pulse oximeter of claim 28, wherein said suspension system comprises a plurality of spring members at least two of which being secured to each of the ledges at a given distance away from each other to provide an evenly distributed biasing upward support force for said non-fixed portion.

30. Pulse oximeter of claim 26, further comprising a circuit board coupled to the upper surface of said fixed portion, electronic components and a display being mounted to said circuit board, said fixed portion having an aperture through which a light from a light emitting device electrically connected to said circuit board passes for illuminating a finger placed below said fixed portion.

* * * * *